United States Patent [19]

Schufeldt

[11] Patent Number: 6,024,839
[45] Date of Patent: Feb. 15, 2000

[54] HYDROQUINONE TO INHIBIT FOULING OF EPICHLOROHYDRIN EQUIPMENT

[75] Inventor: Duane Mark Schufeldt, Webster, Tex.

[73] Assignee: Shell Oil Company, Houston, Tex.

[21] Appl. No.: 08/965,661

[22] Filed: Nov. 6, 1997

[51] Int. Cl.⁷ ............................ B01D 3/34; C07D 301/36
[52] U.S. Cl. .................................. 203/6; 203/8; 549/514; 549/541; 208/48 AA
[58] Field of Search .................................. 203/8, 28, 65, 203/62, 6, 48 AA; 549/514, 541

[56] References Cited

U.S. PATENT DOCUMENTS

| | | | |
|---|---|---|---|
| 4,024,050 | 5/1977 | Shell et al. | 203/6 |
| 4,292,139 | 9/1981 | Rifkin | 203/60 |
| 4,510,041 | 4/1985 | Miller et al. | 208/48 AA |
| 4,927,519 | 5/1990 | Forester | 208/48 AA |
| 4,944,847 | 7/1990 | Snow | 203/8 |
| 5,064,557 | 11/1991 | Fusiak | 252/162 |
| 5,207,874 | 5/1993 | Hess et al. | 203/8 |
| 5,213,678 | 5/1993 | Rondum et al. | 208/48 AA |
| 5,243,063 | 9/1993 | Devicaris et al. | 558/304 |
| 5,663,215 | 9/1997 | Milligan | 523/122 |

FOREIGN PATENT DOCUMENTS

| | | |
|---|---|---|
| 100607 | 9/1982 | European Pat. Off. . |
| 1027997 | 1/1989 | Japan . |
| 9255642 | 9/1997 | Japan . |
| 19710 | 11/1992 | WIPO . |

OTHER PUBLICATIONS

Pro chaska et al. On The Mechanisms of induction of cancer—protective enzymes. Proc. Natl. Acad. Sci. U.S.A. 82 (23), 8232–6 (English) 1985.

*Primary Examiner*—Virginia Manoharan
*Attorney, Agent, or Firm*—Dennis V. Carmen

[57] ABSTRACT

A method of inhibiting fouling of one or more pieces of equipment for processing crude epichlorohydrin by treating at least one epichlorohydrin stream entering or exiting the one or more pieces of equipment with hydroquinone as an antifoulant.

10 Claims, No Drawings

HYDROQUINONE TO INHIBIT FOULING OF EPICHLOROHYDRIN EQUIPMENT

FIELD OF THE INVENTION

This invention relates to inhibiting fouling of equipment for the purification of epichlorohydrin by treating the equipment with an antifoulant comprising hydroquinone.

BACKGROUND OF THE INVENTION

There exists a variety of known methods for the manufacture of epichlorohydrin. These are summarized in U.S. Pat. No. 4,944,847, incorporated herein by reference. This patent describes many commonly used methods for manufacturing epichlorohydrin, such as by reacting an allylchloride with chlorine water to yield an isomeric glycerol chlorohydrin mixture which is dehydrochlorinated with an alkali material to form epichlorohydrin, which is subsequently isolated and purified by steam stripping and distillation. In an alternative method, the chlorohydrin can be made by chlorinating acrolein followed by reduction of the resulting aldehyde to form a dichlorohydrin, which is then dehydrochlorinated to form epichlorohydrin. Other methods include epoxidation of an allylchloride or oxidation of an allylchloride with air.

In each of these processes, a crude epichlorohydrin product containing impurities such as unreacted monomers or byproducts requires subsequent processing to isolate and purify epichlorohydrin. The purification of epichlorohydrin is typically accomplished through a distillation process or by other known separation techniques which produce a stream having a higher concentration of epichlorohydrin than the crude stream treated. In the separation processes, impurities can collect in various parts of the distillation towers or the equipment located downstream from the distillation tower, such as condensers, accumulators, and pipes. As these byproducts and unreacted species flow through the equipment, they can and typically do foul the equipment by undergoing reactions which form a gum. Consequently, the process must be shut down from time to time to clean out the fouled equipment. It is believed that the fouling is due largely to polymerization of one or more impurities distilled and separated from epichlorohydrin.

In an effort to solve this problem, various chemical ingredients have been proposed to inhibit the fouling of equipment used to isolate epichlorohydrin. These ingredients include 2,6-ditertiarybutyl-4-methylphenol, 2,6-ditertbutylphenol, or mixtures thereof commonly sold as antioxidants under the name Ionol, Ethyl 733, and Univox. However, these ingredients were only somewhat effective in retarding the fouling of epichlorohydrin equipment. In U.S. Pat. No. 4,944,847, a $C_3$–$C_9$ linear or branched alkyl substituted catechol, preferably a 4-tertiarybutylcatechol, was proposed as an antifoulant to technically outperform the hindered phenols previously described. Unlike the hindered phenols, this material is quite expensive due to its limited availability. Thus, there remains a need to find an alternative antifouling ingredient which is both technically and commercially competitive.

SUMMARY OF THE INVENTION

It has now been found that hydroquinone is an excellent compound for inhibiting fouling of epichlorohydrin equipment, outperforming 4-tertbutylcatechol on a performance per cost basis. This is due in part to the difference in cost of the materials and blended product. The cost of 99% pure hydroquinone is about half the cost of 85% pure 4-tertbutylcatechol. Accordingly, hydroquinone satisfies the dual role as an attractive commercial and technical alternative to 4-tertbutylcatechol as an antifoulant.

Accordingly, there is provided a method of inhibiting fouling of one or more pieces of equipment for processing crude epichlorohydrin, said method comprising treating at least one epichlorohydrin stream entering or exiting said one or more pieces of equipment with an antifoulant comprising hydroquinone.

DETAILED DESCRIPTION OF THE INVENTION

Hydroquinone is preferably dissolved in a solvent prior to adding the solution to the epichlorohydrin stream. A suitable solvent is any which brings hydroquinone into solution at ambient temperature, remains inert to ingredients in the epichlorohydrin stream with respect to causing such ingredients to polymerize, and does not lower the purity level of the processed epichlorohydrin. It is preferred that the solvent chosen can be stripped from process streams in the overhead of the distillation towers operating in the process for manufacture of epichlorohydrin.

One example of a suitable solvent is an alcohol. Suitable alcohols include branched or unbranched, saturated or unsaturated, substituted or unsubstituted aliphatic alcohols, preferably 1–6 carbon atoms. Mention may be made of methanol, ethanol, propanol or isopropanol, butanol, isobutanol or tertiary butanol and such other alcohols which form solutions with hydroquinone. Isopropanol was used in this study.

Other solvents may also be used, such as low molecular weight polyols (<500$M_n$) alkylene oxides, and the halogenated alcohols and alkanes, especially those produced as byproducts isolated from the manufacture or processing of epichlorohydrin. These alcohols include the chlorinated alcohols such as alpha monochlorohydrin, beta monochlorohydrin, alpha gamma dichlorohydrin, alpha, beta dichlorohydrin, glycerol monochlorohydrin, 1-chloro-2-propanol, 2-chloro-1-propanol, 3-chloro-1-propanol, and the like. These chlorinated alcohols generally contain from 1–6 carbon atoms and at least one chlorine atom along with at least one alcohol functional group.

In addition to the solvents mentioned above, other polar organic solvents may also be used, such as acetone, methyl ethyl ketone, tetrahydrofuran, and the like.

The concentration of hydroquinone to be blended in solution will, of course, depend upon the type of solvent and the ambient temperature of the storage and injection facilities. In general, the hydroquinone solution will have a concentration ranging from 10 wt % to 25 wt %.

The antifoulant used in the invention is hydroquinone, a $C_1$–$C_{12}$ branched or unbranched alkyl substituted hydroquinone, or mixtures thereof, but preferably hydroquinone. The percentage of polymer gum reduced by using hydroquinone as an antifoulant per unit cost per unit volume is between four and five times greater than the percentage of reduction seen when using 4-tertiarybutylcatechol as the antifoulant. Industrially, the amount of hydroquinone will be fed into an epichlorohydrin stream at a rate of about 25 ppm to 250 ppm, more typically from 50 ppm to 200 ppm.

Hydroquinone can be added to various equipment to inhibit fouling. Hydroquinone can be added to distillation towers, reflux lines, overhead lines, and vent lines. It can also be used to inhibit fouling in a water stripper which is used to remove organics from an aqueous epichlorohydrin waste stream. Due to the large boiling point differential between the antifoulant components (hydroquinone and solvent) and epichlorohydrin, the antifoulant will exit the distillation unit with the light ends and heavy ends waste streams rather than the finished epichlorohydrin product.

The epichlorohydrin streams can be in a liquid, gas, or mixed liquid/gas state. The epichlorohydrin streams treated with hydroquinone will contain a wide variety of organic impurities with varying concentrations depending on the stage at which the hydroquinone is added to treat the stream. While the particular stream treated may contain only trace amounts of epichlorohydrin or no epichlorohydrin, it is nevertheless deemed an epichlorohydrin stream within the meaning of the invention if derived from the crude epichlorohydrin stream since byproducts which may possibly foul pipes, vessels or other equipment may remain in the stream even after epichlorohydrin has been removed.

The following examples illustrate the effects of the invention and are not limited thereto.

EXAMPLES

The results of various fouling tests are provided below. The results were obtained using test procedure ASTM D-873-74, a procedure to measure oxidation stability of aviation fuels. The test conditions were as follows. The unit described in the ASTM standard was operated at 100° C. under 100 psig $O_2$ for 1 hour. The 1 hour aging period chosen was sufficient to yield enough gum or fouling material to measure the performance of the antifoulant. Only unwashed gum results were reported. However, there was not a significant difference between unwashed and washed gum results.

The stream tested was obtained from an epichlorohydrin distillation tower and identified as overhead "light ends". The analytical description for this light ends epichlorohydrin stream is presented in Table 1 below.

TABLE 1

| Light Ends composition | |
|---|---|
| Ingredients | Weight Percentage |
| Epichlorohydrin | 20–25 |
| Allyl Chloride | 18–22 |
| Dichloropropene | 10–15 |
| Saturated/Unsaturated Compounds | Remainder |

The saturated/unsaturated hydrocarbons includes chlorinated hydrocarbons, aldehydes, alcohols, alkanes and alkenes, allylic compounds, water, dichlorohydrins, and other byproducts. Variations in both type and amount of impurities in this type of process stream are to be expected, depending on the distillation column parameters and crude feedstock composition at the time the sample is obtained.

A 1 quart light ends sample was shaken and divided by transferring 100 mL into 3 smaller bottles. One bottle was the blank into which no antifoulant was added. To the second bottle was dosed a solution of 4-tertiarybutylcatechol (TBC) dissolved in isopropanol such that the amount of 4-tertiarybutylcatechol solution introduced was 500 ppm. To the third bottle was dosed a solution of hydroquinone dissolved in isopropanol at the same concentration as the TBC solution, and the amount of hydroquinone solution introduced into the bottle was also the same, 500 ppm. 50 ml samples were withdrawn from each bottle and placed into their own bombs at 100 psig in a bath at 100° C. for 1 hour. The formed gum was jet evaporated, and weighed. The results are reported in Table 2 below:

TABLE 2

| Antifoulant | Dosage (ppm) | Gum, mg/100 mL | % Reduction | Approximate Dollar/gallon | % Reduction/Dollar/gallon |
|---|---|---|---|---|---|
| Blank | — | 59.9 | — | — | — |
| 4-Tertbutylcatechol | 500 | 0.8 | 98.7 | 25–35* | 4–2.8 |
| Hydroquinone | 500 | 2.9 | 95.2 | 5–6* | 15.9–19.0 |

*The cost of the antifoulants are from currently available, commercial products

Hydroquinone reduced the level of gum formation to about the same level as 4-tertiarybutylcatechol. This result indicates, without regard to commercial considerations, the use of hydroquinone is a technical alternative to 4-tertiarybutylcatechol. However, considering the large gap in cost, the performance of hydroquinone outweighs the performance of 4-tertiarybutylcatechol by at least five times. This not only provides a commercial advantage, but allows one a wider latitude in the amount of antifoulant added such that two or three or more times the volume of hydroquinone can be added at less than the cost of 4-tertiarybutylcatechol while obtaining a greater percentage reduction in gum formation. The results in Table 3 demonstrate the reductions in gum formation one may obtain when using hydroquinone in larger amounts while staying below the costs of 4-tertiarybutylcatechol. The experiments were performed in the same manner as described above, except that the dosage levels were adjusted as shown in Table 3.

TABLE 3

| Antifoulant | Dosage (ppm) | Gum, mg/100 mL | % Reduction | Approximate Dollar/gallon | % Reduction/Dollar/gallon |
|---|---|---|---|---|---|
| Blank | — | 483.7 | — | — | — |
| 4-Tertbutylcatechol | 250 | 34.4 | 92.8 | 25–35 | 2.7–3.7 |
| Hydroquinone | 500 | 23 | 95.2 | 2*(5–6) | 7.9–9.5 |
| Hydroquinone | 750 | 4.5 | 99.1 | 3*(5–6) | 5.5–6.6 |

The results indicate that one may use three times the amount of hydroquinone over 4-tertiarybutylcatechol at costs still less than that of the catechol and achieve about a 99% reduction in gum formation compared to about a 93% reduction using the catechol.

What I claim is:

1. A method of inhibiting fouling of at least one piece of equipment for processing crude epichlorohydrin, said method comprising treating at least one epichlorohydrin stream entering, contained or exiting said at least one piece of equipment with and antifoulant comprising hydroquinone at a dosage level of from 50 ppm to 750 ppm hydroquinone.

2. The method of claim 1, wherein said at least one epichlorohydrin stream comprises a light ends epichlorohydrin stream obtained by distilling epichlorohydrin with hydroquinone.

3. The method of claim 2, wherein said light ends epichlorohydrin stream is obtained by distilling epichlorohydrin with hydroquinone added at a rate ranging from 50 ppm to 250 ppm.

4. The method of claim 3, wherein hydroquinone is added at a rate of 50 ppm to 200 ppm.

5. The method of claim 1, wherein said hydroquinone is dissolved in an organic solvent and subsequently added to a light end epichlorohydrin distillate stream obtained from distillation of epichlorohydrin.

6. The method of claim 1, said at least one piece of equipment comprising a condenser line and/or a reflux line, further comprising adding said hydroquinone to the condenser line and/or the reflux line.

7. The method of claim 1, wherein said at least one epichlorohydrin stream comprises a crude epichlorohydrin stream entering or contained within a distillation column, and hydroquinone is added to said crude epichlorohydrin stream.

8. The method of claim 1, wherein said hydroquinone is dissolved in an alcohol as a solution having a concentration ranging from 10 percent to 25 percent, prior to treatment.

9. A method of inhibiting fouling of at least one piece of equipment for processing crude epichlorohydrin, said method comprising adding a 10 wt % to 25 wt % hydroquinone solution at a dosage ranging from 50 ppm to 750 ppm hydroquinone to at least one epichlorohydrin stream entering, contained or exiting said equipment.

10. A method of claim 9, wherein said at least one epichlorohydrin stream comprises a crude epichlorohydrin stream entering or contained within a distillation column, and said hydroquinone solution is added to said epichlorohydrin stream.

* * * * *